(12) United States Patent
Andersen

(10) Patent No.: US 9,194,854 B2
(45) Date of Patent: Nov. 24, 2015

(54) AQUATIC POLLUTION MONITORING

(75) Inventor: Odd Ketil Andersen, Stavanger (NO)

(73) Assignee: BiotaTools AS, Stavanger (NO)

( * ) Notice: Subject to any disclaimer, the term of this patent is extended or adjusted under 35 U.S.C. 154(b) by 581 days.

(21) Appl. No.: 13/577,180

(22) PCT Filed: Feb. 7, 2011

(86) PCT No.: PCT/GB2011/050209
§ 371 (c)(1),
(2), (4) Date: Oct. 11, 2012

(87) PCT Pub. No.: WO2011/095827
PCT Pub. Date: Aug. 11, 2011

(65) Prior Publication Data
US 2013/0118236 A1   May 16, 2013

(30) Foreign Application Priority Data

Feb. 5, 2010 (GB) .................................. 1001957.8

(51) Int. Cl.
*G01N 33/18* (2006.01)
*G01N 21/63* (2006.01)

(52) U.S. Cl.
CPC .............. *G01N 33/18* (2013.01); *G01N 33/186* (2013.01); *G01N 2021/635* (2013.01)

(58) Field of Classification Search
CPC .......... G01N 2015/088; G01N 33/186; G01N 33/1866
See application file for complete search history.

(56) References Cited

U.S. PATENT DOCUMENTS 6,119,630 A    9/2000 Lobsiger et al.
2003/0211041 A1* 11/2003 Ezratty et al. ................. 424/9.2

FOREIGN PATENT DOCUMENTS

WO   2007/086754 A1   8/2007
WO   2009/013503 A1   1/2009
WO   2011/064595 A1   6/2011

OTHER PUBLICATIONS

T. Stromgren, "Linear Measurements of Growth of Shells Using Laser Diffraction," Limnology and Oceanography, Jan. 1, 1975, pp. 845-848, vol. 20, No. 5, Grafton, WI, US.
T. Stromgren, "The Combined Effect of Copper and Hydrocarbons on the Length Growth of *Mytilus edulis*," Marine Environmental Research, Jan. 1, 1986, pp. 251-258, vol. 19, No. 4, Elsevier Applied Science Publishers, GB.
S. Lefloch, et al., "Effects of Oil and Bioremediation on Mussel (*Mytilus edulis* L) Growth in Mudflats," Environmental Technology, Oct. 1, 2003, pp. 1211-1219, vol. 24, No. 10, Selper Ltd., GB.
A. R. Manley, et al., "The Effect of Copper and Zinc on the Shell Growth of *Mytilus edulis* Measured by a Laser Diffraction Technique," Journal of the Marine Biological Association of the United Kingdom, Jan. 1, 1984, pp. 417-427, vol. 64, No. 2, Cambridge University Press, GB.

(Continued)

*Primary Examiner* — Paul West
(74) *Attorney, Agent, or Firm* — Hall Estill Attorneys at Law

(57) ABSTRACT

The effects of pollution in an aquatic mass may be monitored by measuring changes in various parameters of sessile organisms, particularly bivalves such as mussels. Particular parameters measured include particle clearance rate, oxygen consumption and apical growth.

38 Claims, 6 Drawing Sheets

(56) References Cited

OTHER PUBLICATIONS

P. C. Almada-Villela, et al., "The Effects of Temperature on the Shell Growth of Young *Mytilus edulis*," Journal of Experimental Marine Biology and Ecology, Jan. 1, 1982, pp. 275-288, vol. 59, No. 2-3, Elsevier Biomedical Press, Amsterdam, NL.

LL. D. Gruffydd, et al., "The Reduction Growth of *Mytilus edulis* in Fluctuatingi Salinity Regines Measured Using Laser Diffraction Patterns and the Exaggeration of This Effect by Usinig Tap Water as the Diluting Medium," Journal of the Marine Biological Association of the United Kingdom, Jan. 1, 1984, pp. 401-409, vol. 64, No. 2, Cambridge University Press, GB.

H. Sushko, et al., "The Use of Laser Diffraction in Measuring the Effect of Suspended Sediment on the Shell Growth of Mussels *Mytilus edulis*," Canadian Manuscript Report of Fisheries and Aquatic Sciences, Jan. 1, 1991, 31 pps., No. 2121, CA.

T. Stromgren, et al., "Growth in Length of *Mytilus edulis* Fed on Different Algal Diets," Journal of Experimental Marine Biology and Ecology, Jan. 1, 1984, pp. 23-34, vol. 76, No. 1, Elsevier, Amsterdam, NL.

. "Coral Growth: Lawer Based Underwater and Laboratory Measurements," http://www.aims.gov.au/pages/laser2.html, (page accessed Nov. 21, 2007).

R. Vago, et al., "Laser measurements of coral growth," Nature 386, 1997, pp. 30-31.

T. Stromgren, "Growth Rates of *Modiolus americanus* (Leach) in Relation to Mechanical Disturbance and Darkness," Bulletin of Marine Science 26(3), 1976, pp. 410-413.

T. Stromgren, "Temperature-length Growth Strategies in the Lottoral Alga *Ascophyllum nodosum* (L)," Limnology and Oceanography 28(3), 1983, pp. 516-521, The American Society of Limnology and Oceanography, Inc.

T. Sgromgren, "Skeleton Growth of the Hydrocoral *Millepora complanata* Lamarck in Relation to Light," Limnology and Oceanography 21(1), 1976, pp. 156-160.

S. Nixon, "Science: Laser Sheds Light on How Coral Grows," New Scientist magazine, Mar. 8, 1997, p. 16.

S. Nicholson, et al., "Pollution monitoring in Southeast Asia using biomarkers in the mytilid mussel *Perna viridis* (Mytilidae: Bivalvia)," Environment International, Jan. 1, 2005, pp. 121-132, vol. 31, No. 1, Pergamon Press, US.

S. Nicholson, "Cardiac and branchial physiology associated with copper accumulation and detoxication in the mytilid mussel Pema viridis (L.)," Journal of Experimental Marine Biology and Ecology, 2003, pp. 157-171, Elsevier.

* cited by examiner

AQUATIC POLLUTION MONITORING

This invention relates to improvements in and relating to methods of monitoring pollution in an aquatic mass, and to apparatus for use in such methods.

Pollution of aquatic masses, e.g. oceans, seas, lakes and rivers, may arise through an accidental spill, or as a consequence of a deliberate discharge either of which take the form of the release into the aquatic mass of chemicals which affect the ability of the indigenous flora and fauna to thrive. In the case of deliberate discharges, these may be legally permitted but nonetheless eventually prove unexpectedly to be harmful. In the case of fixed installations which may be liable to be alleged to be a pollution source, as well as for operators of fixed installations which may suffer detrimental effects from aquatic pollution, it is desirable for the aquatic mass to be monitored to detect pollution events in order that compensatory or protective action may be taken or in order to demonstrate that in fact legal compliance has been achieved. Such installations will typically comprise offshore drilling or hydrocarbon recovery installations, ports and other land/water material transfer locations, land-based industrial, municipal, and private discharges, fish farms and the like. Pollution detection can also be helpful in identifying previously unknown side-effects of legal discharges.

Many multi-cellular non-mammalian aquatic animals, e.g. fish, shellfish, etc. exhibit detectable changes in physiology/behaviour in response to exposure to pollution which are far more sensitive and relevant than simply measuring death. Such behaviour includes alteration of growth rate, alteration of heart beat and alteration in shell opening and closing behaviour. The use of such animals, so-called "indicator" or "sentinel" species, in real time environmental monitoring (RTEM) methods is widely known and is described for example in WO 2007/086754 and WO 2009/013503, the contents of which are incorporated herein by reference. An important advantage of RTEM methods is that they are non-invasive.

Two systems have evolved which have been used on marine organisms, one based on physiological responses (heart rate monitoring), the other based on behaviour (valve gaping in mussels). However, such systems are most responsive to acute incidents rather than long term, low dose responses. There still exists a need to develop RTEM methods that can directly measure important parameters sensitive to low dose chronic exposure situations used in environmental risk assessment and management and which will reduce the use of invasive methods as biomarkers in environmental monitoring. The present invention seeks to address this need and, in particular, to provide alternative methods of directly monitoring aquatic animals which can be used to monitor pollution both in the short and longer term.

When viewed from a first aspect the present invention provides a method of monitoring the effect of pollution in an aquatic mass, said method comprising:
 disposing in said aquatic mass a biosensor unit containing a living sessile organism;
 performing a series of first measurements, of a flux of particles in said aquatic mass in a region adjacent a feeding orifice of said organism;
 performing a series of second measurements, of a flux of particles in said aquatic mass in a region adjacent an excretion orifice of said organism; and
 using said first and second measurements to calculate a particle clearance rate for said organism.

When viewed from a second aspect the present invention provides an apparatus for monitoring the effect of pollution in an aquatic mass, said apparatus comprising:
 a biosensor unit containing a living sessile organism;
 means for performing a series of first measurements, of a flux of particles in said aquatic mass in a region adjacent a feeding orifice of said organism;
 means for performing a series of second measurements, of a flux of particles in said aquatic mass in a region adjacent an excretion orifice of said organism; and
 means for calculating a particle clearance rate of said organism using said first and second measurements.

Thus it will be seen by those skilled in the art that in accordance with the invention the particle clearance rate of a sessile organism is used as a non-invasive, in-situ indicator of pollution since the applicant has appreciated that the particle clearance rate is a strong indicator of the organism's scope for growth, which in turn is a good indicator of aquatic pollution. Scope for growth (SFG) is the energy budget of an organism calculated by measuring food uptake (clearance rate), excretion (faecal production) and oxygen consumption. However it has been found that the scope for growth is dominated by the clearance rate (e.g. of the order of: clearance rate 50-60%, faecal production 10-20% and oxygen consumption 15-25%). It is feasible therefore to measure just the clearance rate in place of SFG. The SFG or clearance rate is a strong and sensitive method of showing the effect of pollution directly in an aquatic mass.

The flux of particles could simply be defined as the number of particles passing through a given planar area in a given time, but in preferred embodiments the size distribution is also measured. By taking the size distribution into account an estimate of the mass and/or volume flux can be made which gives a more accurate picture of the potential food value. By examining the fluxes measured adjacent the intake of the organism and adjacent its outflow respectively, the uptake of food by the organism, i.e. the clearance rate can be calculated.

It follows from the above that the particle clearance rate calculated in accordance with the invention could take a number of forms. It could be the number of particles retained by the organism in a given time or from a given volume of water in which the particles are suspended that passes through the organism. Alternatively it could be the aggregate size or volume of particles retained in a given time. However there are other possibilities such as the number of particles over a predetermined size or within a predetermined range of sizes that are retained in a given time or suspension volume.

The particles monitored in accordance with the invention will typically be food particles such as plankton. It is even envisaged that the measurements could identify particles of different types and either exclude some particles from the calculations (e.g. particles of non-food debris) or attach different weightings to different particles in the calculations. These different weightings could be based on many factors or combination of factors such e.g. the food value.

The Applicant has recognised that it is not always essential to measure actual particle fluxes on either side of the organism. In some circumstances it may be sufficient to make assumptions about the density of food particles in the surrounding water in which case the apparatus could be arranged simply to measure the pumping rate of the organism, that is the rate at which ambient water passes through it. The assumed density of food particles could be measured periodically or it may even be assumed to remain relatively constant such that pumping rate is just used a proxy for clearance rate.

When viewed from a further aspect therefore the invention provides a method of monitoring the effect of pollution in an aquatic mass, said method comprising:

disposing in said aquatic mass a biosensor unit containing a living sessile organism;

performing a series of first measurements, of a flow of water in a region adjacent a feeding orifice of said organism;

performing a series of second measurements, of a flow of water in a region adjacent an excretion orifice of said organism; and using said first and second measurements to calculate a pumping rate for said organism.

When viewed from another aspect the present invention provides an apparatus for monitoring the effect of pollution in an aquatic mass, said apparatus comprising:

a biosensor unit containing a living sessile organism;

means for performing a series of first measurements, of a flow of water in a region adjacent a feeding intake orifice of said organism;

means for performing a series of second measurements, of a flow of water in a region adjacent an outflow orifice of said organism; and means for calculating a pumping rate of said organism using said first and second measurements.

Whilst it is possible in accordance with all the foregoing aspects of the invention to measure volume flow rates directly—i.e. the volume of particles or volume of water passing per unit time—this is not essential. In a set of embodiments an estimate of the volume flow rate is achieved by measuring the flow speed of the water. For a given siphon cross-section which the organism presents, this will be proportional to the volume flow rate. Since in accordance with at least some embodiments of the invention only changes in the particle clearance rate are important, this may be sufficient. Alternatively the cross-sectional area may be estimated or measured to yield an estimate of the actual volume flow rate.

The Applicant has appreciated that in practice the siphon cross-sectional area of the organism will depend on the degree of gaping—i.e. whether the mussel or other organism is fully open. It can either be assumed that this is the case (or at least that this will be the case over a measurement cycle and therefore that a maximum flow speed should be used) or the degree of gaping may be measured. One way of doing this is described in "A fiber optic sensor for high resolution measurement and continuous monitoring of valve gape in bivalve molluscs" Journal of Shellfisheries Research, August, 2007 by Dana M. Frank, John F. Hamilton, J. Evan Ward, Sandra E. Shumway.

Thus the flow rates from which the pumping rate is calculated could be measured in a variety of ways—e.g. with a separate sensor, but in a set of embodiments the pumping rate is determined using the velocity vectors of particles carried in the water. In one possible set of embodiments a set of sensors could be used continuously or frequently to measure water flow speed, which inherently requires relatively less processing power, and periodically or less frequently also to determine particle density, which requires relatively greater processing. Water flow rate (via flow speed) could for example be measured locally with particle density be calculated from analysis carried out remotely.

Measurements of particle density or flux may be carried out in a number of different ways. For example, one or more bulk properties of the volume of water could be measured such as the transmissivity, reflectivity or absorbance of the water to light, other electromagnetic radiation or sound; combined with knowledge obtained either theoretically or empirically as to how the density or flux influences sensors. Alternatively the change in frequency distribution of a signal emitted into the water after transmission or reflection through the volume being measured could be determined.

In a set of preferred embodiments however, measurements of individual particles are carried out. There are again a number of techniques which could be used. The water could be imaged and image processing techniques used to locate individual particles. In some preferred embodiments a laser particle detector is employed. Suitable examples include a miniature laser Doppler velocimeter (mini-LDV), laser Doppler anemometer (LDA), particle image velocimeter (Ply), or a time-of-flight velocity sensor. Suitable sensors are available commercially from Measurement Science Enterprise, Inc. of Pasadena, Calif. or Dantec Dynamics of Skovlunde, Denmark. These sensors can of course carry out simple water flow speed measurements referred to above either in addition to or instead of particle density/flux measurements.

Sessile organisms suitable for use in the invention include filter feeders, ascidians sponges and bivalves such as mussels, scallops, clams, etc.

Although the methods herein described may be performed on a single organism, it is preferred that these are carried out simultaneously or sequentially on a plurality of organisms from the same species. In this way, accuracy of the monitoring methods may be improved by measuring the clearance rate of a statistically significant sample. In such embodiments a common radiation source and/or detector are preferably employed. For example the apparatus could be arranged to bring a radiation-and-detector arrangement into successive mutual alignment with each of a plurality of organisms.

In an exemplary embodiment, a plurality of sessile organisms may be distributed around the rim of a disc or the outer surface of a cylinder. Each may be associated with its own detector, or one or more detectors may be shared between a greater number of organisms, in which case a mechanical arrangement could be employed to move the sensor or organism into mutual proximity for conducting measurements. In a set of preferred embodiments, one or more detectors is arranged to measure the particle flux or density in the common environment of all the organisms, from which they draw in their food, whereas each organism is provided with its own detector to detect its exhaled particle flux or density or flow speed. The cylinder is preferably transparent so that optical detectors may be disposed on the opposite side thereof. It is preferably sealed so that detectors may be placed in a dry environment or embedded in the cylinder wall.

The Applicant has appreciated that for algal particles, one way of measuring particle flux in flow to measure clearance rate is to measure the concentration of chlorophyll a in the region of the feeding and excretion orifices respectively. This can be done by measuring chlorophyll a fluorescence. Thus in one set of embodiments the apparatus comprises means for measuring chlorophyll a fluorescence in the region of the feeding and excretion orifices of the organism respectively.

This is novel and inventive in its own right and thus when viewed from a further aspect the invention provides a method of monitoring the effect of pollution in an aquatic mass, said method comprising: disposing in said aquatic mass a biosensor unit containing a living sessile organism;

performing a series of first measurements, of chlorophyll a fluorescence in said aquatic mass in a region adjacent a feeding orifice of said organism;

performing a series of second measurements, of chlorophyll a fluorescence in said aquatic mass in a region adjacent an excretion orifice of said organism; and using said first and second measurements to calculate a particle clearance rate for said organism.

When viewed from another aspect the present invention provides an apparatus for monitoring the effect of pollution in an aquatic mass, said apparatus comprising:

a biosensor unit containing a living sessile organism;

means for performing a series of first measurements, of chlorophyll a fluorescence in said aquatic mass in a region adjacent a feeding orifice of said organism;

means for performing a series of second measurements, of chlorophyll a fluorescence in said aquatic mass in a region adjacent an excretion orifice of said organism; and means for calculating a particle clearance rate of said organism using said first and second measurements.

In a set of embodiments at least one further sensor is employed in association with the or each organism in order to detect a different pollution-dependent characteristic thereof. As mentioned above, one such alternative to clearance rate is oxygen consumption of the organism which can be measured to infer metabolism. This can be used for environmental monitoring of pollution effect of the type taught herein since metabolic rate exhibits an reversed relationship with pollution. This is novel and inventive in its own right, without necessarily requiring measurement of clearance rate, and thus when viewed from a yet further aspect the invention provides a method of monitoring the effect of pollution in an aquatic mass, said method comprising: disposing in said aquatic mass a biosensor unit containing a living sessile organism;

performing a series of first measurements, of oxygen concentration in said aquatic mass in a region adjacent a feeding orifice of said organism;

performing a series of second measurements, of oxygen concentration in said aquatic mass in a region adjacent an excretion orifice of said organism; and using said first and second measurements to calculate an oxygen consumption rate for said organism.

When viewed from yet another aspect the present invention provides an apparatus for monitoring the effect of pollution in an aquatic mass, said apparatus comprising:

a biosensor unit containing a living sessile organism;

means for performing a series of first measurements, of oxygen concentration in said aquatic mass in a region adjacent a feeding orifice of said organism;

means for performing a series of second measurements, of oxygen concentration in said aquatic mass in a region adjacent an excretion orifice of said organism; and means for calculating an oxygen consumption rate of said organism using said first and second measurements.

In another exemplary set of embodiments comprising a plurality of different types of sensor, the apparatus comprises a sessile organism exhibiting apical growth bound thereto, an edge so as to form a gap between it and a tip of the sessile organism, an electromagnetic source arranged such that a beam therefrom impinges upon said gap to produce a diffraction pattern, and a corresponding electromagnetic detector arranged to detect said diffraction pattern and means for monitoring a change in said diffraction pattern over time which is indicative of the natural growth of the apical tip of said organism. Such embodiments are beneficial as they exploit the dependence of two parameters: clearance rate/pumping rate and apical growth on the level of environmental pollution. This can allow more accurate indications to be given either where an indication from one parameter can act as validation of the other, or where the two parameters have different (albeit likely overlapping) sensitivities in terms of pollutant substances, concentration sensitivity, or response time-scales.

More generally when viewed from a further aspect the invention provides a method of monitoring the effect of pollution in an aquatic mass, said method comprising:

disposing in said aquatic mass a biosensor unit containing a living sessile organism;

performing measurement of a first pollution-sensitive parameter of said organism;

performing measurement of a second pollution-sensitive parameter of said organism; and generating a signal indicating the presence of pollution on the basis of said measurements of said first and second parameters.

The first and second pollution-sensitive parameters are preferably selected from the group comprising: apical growth rate, particle clearance rate, food uptake rate, pumping rate, scope for growth, faecal production, oxygen consumption, heart rate, shell opening frequency and shell opening duration.

As mentioned above, a set of preferred embodiments is arranged to measure apical growth of the organism(s). Measurement of growth is a central and sensitive parameter in environmental risk assessment. In terms of animal growth as an indicator of pollution, measurement of apical growth (i.e. growth along a defined axis) is particularly appropriate. Apical growth includes, for example, shell size growth of sessile organisms, especially filter feeders such as bivalves (e.g. mussels, clams and scallops).

However, while these measurements can be carried out in the laboratory with ease, automated monitoring of shell growth in situ within the aquatic mass being monitored is less straightforward. The use of real time environmental monitoring (RTEM) in the sea provides additional challenges with regard to in situ deployment due to its corrosive environment. Nonetheless, the Applicant has now found that RTEM may effectively be carried out on various marine organisms, such a bivalves, using methods which involve light diffraction. In particular, it has been found that changes in diffraction patterns which are dependent on the separation of an organism which exhibits apical growth and an adjacent structure (edge) can be used to measure apical growth of the organism. This in turn is able to provide a direct indication of aquatic pollution.

Thus in accordance with some preferred embodiments of the invention when the gap between the edge and the apical tip of the sessile organism (e.g. the tip of its shell) is sufficiently small, electromagnetic radiation passing through to the detector will form a diffraction pattern (when the diameter of the gap is of the order of the wavelength of the incident light). This in turn will be noticeable above the background light detected by the detector, e.g. as spikes or 'maxima' in the spatial radiation intensity detected across the detector. As the organism grows and the gap is narrowed so the diffraction pattern changes—the maxima become more widely separated. Such changes can be related to the change in slit width and thus the extent of growth of the sessile organism. Thus in turn can be related to the presence or concentration of pollution in the aquatic mass.

Any suitable electromagnetic radiation source can be employed depending upon the sensitivity required. In preferred embodiments the source is a light source although it need not be in the visible range—e.g. the source may have a wavelength between 10 nm and 10 microns, preferably between 300 nm and 800 nm. Unless otherwise specified the term "light" as used herein is not to be taken as limiting the invention to any particular wavelength range.

In preferred embodiments the source is monochromatic in order to make the diffraction pattern as clear as possible. Preferably the source is coherent, preferably comprising a laser. A laser diode or any other suitably compact laser cavity could be employed. Suitable light for use in the invention may be generated by a low energy laser such that there is no harmful effect on the organism. A Ne—He gas laser with a wavelength of 632.7 nm is particularly suitable.

Apical tip growth can be monitored with the carrier in a stationary position until the sessile organism has grown sufficiently for the slit between the apical tip and edge to decrease sufficiently that the diffraction pattern is no longer detectable (either because it has become too faint or the central maximum has expanded to cover the whole detector surface). In some embodiments the carrier and edge are moveable relative to one another in order that the slit can be re-enlarged until a diffraction pattern appears once more. The sessile organism again grows to decrease the slit sufficiently to cause a change in the diffraction pattern and, ultimately, to cause the diffraction pattern to no longer be detectable. If, in successive temporally spaced determinations, the distance between the edge and the apical tip are determined, then these correlate to the apical tip growth (e.g. shell growth) between the temporally spaced determinations.

Where the organism itself is moveable the sensor(s) detecting exhaled particle flux or density could be arranged to be moved in consequence, although it may be that any such movement to compensate for shell growth is insufficient to have a material impact on the particle flux/density measurement and thus compensatory movement may not be necessary.

In carrying out the method of the above-mentioned preferred embodiments of the invention, it is preferred that the apical tip of the sessile organism is initially disposed at a pre-determined distance from the edge such that the resulting slit diameter provides a predetermined diffraction pattern. This could be a diffraction pattern having a predefined number of maxima/minima, a predetermined intensity for any given maximum, a predetermined contrast ratio between any maximum and any minimum etc, or indeed any combination of these. The width of the slit formed between the edge and the apical tip which provides such a diffraction pattern will vary depending on factors such as the wavelength of light which is used, the separation of the slit and the sensor, etc. but may readily be determined by those skilled in the art. Typical widths (edge to apical tip separation) which may provide the predetermined diffraction pattern may lie in the range 100 to 900 μm.

Advantageously, the method of the above-mentioned preferred embodiments of the invention enables long term growth of the sessile organism to be monitored. As described above, in a set of embodiments, this may be achieved by disposing the organism or edge on a movable carrier which can be moved away from the edge or organism respectively in order to carry out further diffraction measurements over any desired period (e.g. several days, months, etc.). The carrier could be moved away from the edge when the separation between the apical tip of the organism and the edge has reduced below a predetermined threshold e.g. less than 200 μm (note that in order not to damage the edge, it is preferred that the apical tip and the edge should not physically come into contact with one another) or at predetermined time intervals, which may be dependent on time of year or on previously measured growth rates. Equally movement of the carrier could be prompted simply by the separation becoming too small to give a detectable diffraction pattern. Preferably movement of the carrier is carried out automatically. The length of time taken for the organism to grow sufficiently that the diffraction pattern diminishes will depend on the nature of the organism, the extent of any pollution, etc. In the case of bivalves, such as mussels, this may be expected to take in the region of 1-2 months.

In a preferred set of embodiments, the method of the above-mentioned preferred embodiments of the invention thus further comprises the step of moving said organism and said edge away from one another when the diffraction pattern is no longer detectable. Preferably, the organism and edge are separated until the detector detects once more a diffraction pattern, preferably a predetermined diffraction pattern as herein defined.

It will generally be preferred to monitor apical tip growth at regular intervals rather than continuously. For example, measurements may be taken at pre-determined time intervals, for example, daily, every 12 hours or, in some cases, more frequently than this, e.g. hourly. The time intervals can be adjusted as required depending on the considered risk of pollution. Measurements of apical growth could be interspersed with other measurements such as those of particle flux/density for calculating clearance rate.

Which sessile organisms are suitable for use in a given embodiment of the invention depends on the parameters being measured. As mentioned previously, those suitable for measuring clearance rate include filter feeders, especially bivalves, such as mussels, scallops, clams, etc. These bivalves are also suitable for measuring apical growth, typically measured at the apex (lip) of the shell and are thus particularly preferred for use where these two measurements are to be carried out. Preferably the sessile organism of which growth is to be measured is a young individual in the growth phase.

Organisms which possess shells may be mounted on the carrier using known methods, e.g. using non-toxic adhesive, cement, filament tape, etc. If apical growth of sessile organisms which do not possess shells is to be measured, known methods may be used to secure the organisms in place, e.g. living algae can be clamped in position on a carrier and coral can be attached to a carrier with filament tape The radiation detector for the apical growth measurement may comprise any convenient apparatus which is able to detect the spatial distribution of the light or other radiation. Where visible or near-visible light is used a charge-coupled-device (CCD) could be used. As an alternative a sweeping or scanning arrangement could be employed. This gives the potential for a greater field of view and thus permits smaller gaps to be observed which in turn allows greater precision in the measurement of the apical growth of the organism. For example the detector could be moveable in a direction parallel to the radiation beam. Alternatively it may take the form of a static, detector with a moving reflector positioned between it and the light source, e.g. an oscillating mirror. In order to enhance the sensitivity to relatively faint non-zero order diffraction maxima it may be desirable in some embodiments to suppress the zero-order maximum either physically with a beam stop (e.g. a light absorber or reflector) or in the detector.

A diverging lens can optionally be included in the path of the diffracted light to allow a shorter distance between the gap and the detector for a given detector resolution.

The edge referred to will be provided by an inert surface up to which the apical tip may grow so as to narrow the gap between apical tip and edge. The edge is preferably provided by a blade, e.g. a narrow sheet positioned at least partially and preferably substantially perpendicular to the light path from light source to light detector (or deflector if a deflector is used). The blade may comprise any suitable material, but typically may be made from a non-corrosive material, such as plastic.

In a set of preferred embodiments, the sessile organism is mounted on a carriage movable towards or away from the edge, e.g. under the influence of a drive motor. The distance the carriage is moved away from the edge may be determinable. This can be achieved in many ways, for example by the use of a threaded screw and a corresponding threaded nut with one attached to the drive motor—the number of rotations required defines the distance moved. Alternatively, a toothed track and a cooperative rotatable cog wheel could be used or a hydraulic system with a control pump. Such mechanical components of the biosensor are preferably provided in a dry (i.e. water-free) part of the system e.g. with a hydraulic connection to the carriage on the outside.

As mentioned previously, a biosensor unit may be provided with a plurality of sessile organisms—e.g. around a disc or cylinder—from which measurements of different pollution-sensitive parameters can be made. In a set of such embodiments each organism may be provided with a corresponding radially separated edge. Each organism may be bound to a movable carriage. The light source for apical growth measurement may then be distributed between each gap via the use of one or more optical fibres. Where a single optical fibre is used to deliver the light, this should be mounted in such a way that this can be manipulated (either manually or, more preferably, automatically) to successively distribute the light beam between each gap. Preferably, the growth of a statistically significant sample is measured, especially preferably 4-20 organisms, particularly 5-10, e.g. 8.

To allow for bivalve growth in other dimensions than shell tip growth, where necessary a further drive mechanism may be provided to allow the shell tip to be aligned with the edge. Cameras can be used to monitor shell position, and the further drive mechanism then operated to achieve the desired alignment.

To ensure a bivalve shell is closed during shell tip growth measurements, the apparatus used is preferably provided with means to induce shell closing, for example a noise, water motion or vibration generator, which may be activated shortly before measurements are made. A camera can be used to observe opening and closing of the shell.

The apparatus in accordance with any aspect of the invention can be used with a single sensor, but in preferred embodiments a plurality of sensors is associated with each organism. These could, for example be selected from the group comprising sensors for measuring water flow speed, particle flow speed, particle flux, chlorophyll a fluorescence, oxygen concentration and apical shell growth.

As time progresses, new sessile organisms may be required and so the apparatus used is preferably configured such that the organism(s) is/are provided on a replaceable module.

In some embodiments the apparatus includes a water sampler so that retrieval of a unit also allows retrieval of temporally spaced water samples for later chemical or biochemical analysis. Such units may readily be cleaned, refitted with a fresh sessile organism and reinstalled.

The apparatus could be provided on any suitable structure depending upon how it is intended to be employed. In some embodiments the components of the apparatus are housed in a water-pervious cage.

The data collected in the biosensor unit could be stored locally for subsequent retrieval but preferably the apparatus comprises data transmission means for transmitting said date to a remote receiver. Any suitable method of data transmission could be employed e.g. a cable, radio, microwave, sonar transmission. The remote receiver typically comprises a computer, e.g. one on or in the installation being monitored. The computer is desirably arranged to generate a signal indicative of the occurrence or non-occurrence of a pollution event. That signal may be generated using signals from the biosensor unit, optionally combined with signals from other sensors, e.g. sensors on or in the installation being monitored.

The sensor unit is preferably also provided with at least one of the following monitors: a temperature monitor; a light monitor; a sound monitor; a salinity monitor; an alkalinity monitor; and a water-flow monitor. The unit preferably also comprises anchoring means and signal transmission means, e.g. a data cable or a radio transmitter.

It is particularly preferred that a plurality of such sensor units as have been described herein be used to monitor an installation and that these be arranged around the installation (if offshore), offshore of the installation (if on shore) or in a freshwater lake or river. Desirably such sensor units are placed upstream and downstream of the installation. Also desirably such sensor units may be arranged both near surface and near bed (i.e. near sea-bed, lake-bed, river bed, etc.).

The signal generated by the computer indicative of the occurrence or non-occurrence of a pollution event may be continuous, regular or on occasion of an event. Moreover, it may be quantitative, semi-quantitative or qualitative. Thus for example it may simply indicate that current conditions are normal, that a specific event has occurred, or that an ongoing discharge is in fact having an effect on the environment. Desirably the signal will indicate the timing, severity and location of an event or the severity of the environmental impact of a discharge. In this way, the installation operator or the monitor of the installation's operations is alerted to take action, e.g. to discern the cause of the abnormal response and to ensure that further operation is in accordance with a "zero effect" policy.

The Applicant has appreciated that environmental impact can be assessed effectively by examining the envelope of measurements of particle clearance rate against particle concentration and/or temperature and specifically changes therein over time. This recognises that whilst the clearance rate may be affected by the degree of valve gape, the maximum measurement is dependent on the level of pollution. Specifically the Applicant has realised that the effect of pollution is that for a given particle concentration or temperature the maximum clearance rate observed across a series of measurements is reduced as compared to when there is no, or less, pollution present: in other words pollution restricts the aforementioned envelope. Accordingly a preferred set of embodiments of the disclosed methods of monitoring the effect of pollution in an aquatic mass comprise the steps of:

carrying out a series of first measurements of particle clearance rate during a first time period;
recording each of said first measurements with an associated measurement of a second parameter to give a series of first data points;
determining and recording a first upper envelope with respect to particle clearance rate for said first data points;
carrying out a series of second measurements of particle clearance rate during a second time period;
recording each of said second measurements with an associated measurement of a second parameter to give a series of second data points;
determining and recording a second upper envelope with respect to particle clearance rate for said second data points; and
comparing said first and second upper envelopes to determine the presence of pollution during said first or second time period.

Similar sets of embodiments utilise the pumping rate, the growth rate or the oxygen consumption respectively in place of the particle clearance rate, Such a method is novel and inventive in its own right and thus when viewed from another aspect the invention provides a method of monitoring the effect of pollution in an aquatic mass comprise the steps of:

placing a living sessile organism in said aquatic mass;
carrying out a series of first measurements of a first parameter of said organism during a first time period;
recording each of said first measurements with an associated measurement of a second parameter to give a series of first data points;
determining and recording a first upper envelope with respect to said first parameter for said first data points;
carrying out a series of second measurements of said first parameter of said organism during a second time period;
recording each of said second measurements with an associated measurement of a second parameter to give a series of second data points;
determining and recording a second upper envelope with respect to said first parameter for said second data points; and
comparing said first and second upper envelopes to determine the presence of pollution during said first or second time period,
wherein said first parameter comprises particle clearance rate, pumping rate or growth rate.

The second parameter may be particle concentration or temperature or any other suitable parameter. The first and second data points could be two-dimensional—i.e. comprising one second parameter, three dimensional—i.e. comprising two parameters other than particle clearance rate, or higher dimensional. In the case of two-dimensional data points the upper envelope is a line, whereas in the case of three-dimensional data points the upper envelope is a surface.

If pollution is determined this may cause an alarm or alert to be triggered. Pollution is indicated by a lower upper envelope. This could occur in either the first of the second time period—i.e. the method could be used to detect to appearance or disappearance of pollution. In some embodiments a quantitative measure of pollution may be determined through a known or empirically-established relationship with the amount by which the upper envelope is reduced.

In accordance with all aspects of the invention it is preferred that data relating to individual organisms is analysed separately from that relating to other individual organisms. This stems from the recognition that the change in the behaviour of any given individual is the most sensitive indicator of the effect of pollution, rather than changes in aggregated or averaged behaviour of a plurality of organisms.

Embodiments of the invention will now be described with reference to the accompanying drawings, in which.

Figure 1:
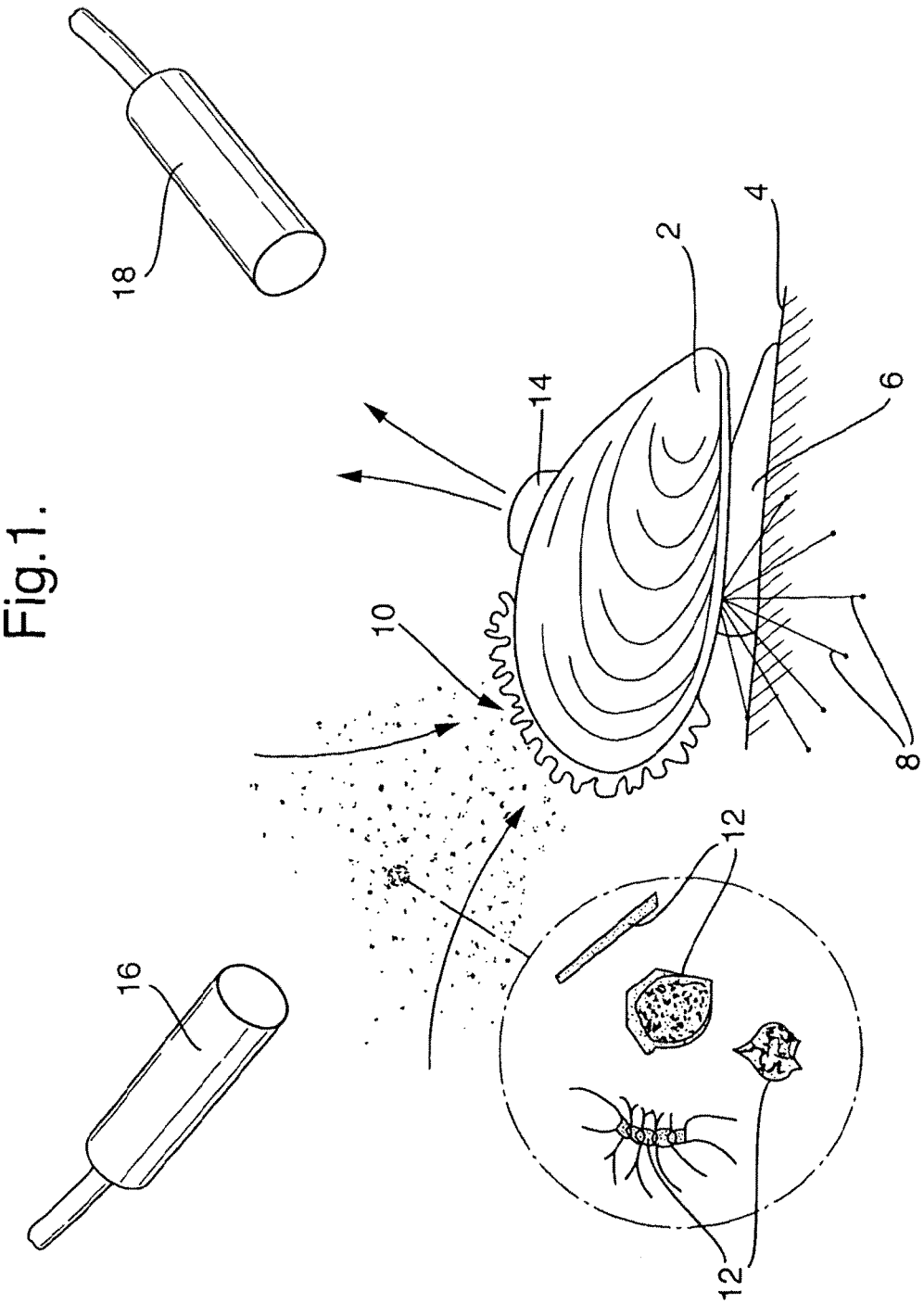
FIG. 1 is a schematic view illustrating the principle of measurement of the clearance rate of a mussel.

FIG. 1 shows a mussel 2 which is a filter feeder bivalve sessile organism. It is attached to a surface 4 by means of its foot 6 and byssus threads 8. At the rounded end of the mussel 2 is an inhalant siphon 10 which sucks in water in which particles including plankton 12 are suspended. The mussel 2 has an exhalant siphon 14 along its upper edge.

Figure 2:
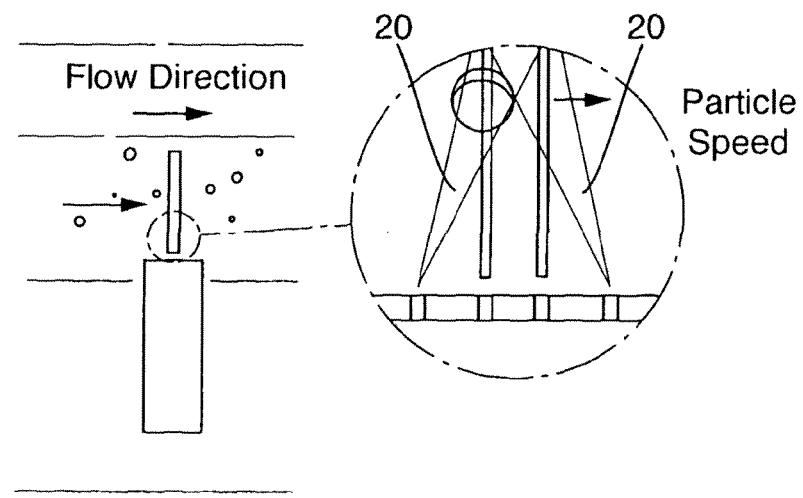
FIG. 2 is a diagram illustrating the principle on which the detectors of one particular embodiment operate.

Two particle flux sensors 16, 18 are disposed in the vicinity of the inhalant siphon 10 and the exhalant siphon 14 respectively. Many different types of sensors could be used but in one example they are 'micro-V' sensors available from Measurement Science Enterprise, Inc. of Pasadena, Calif. However neither the type of sensor nor the manufacturer is essential. As illustrated in FIG. 2, these particular sensors operate by measuring the respective reflections of a pair of spaced laser beams 20 from a particle passing through a particular volume of water. The reflections can be used to estimate the size of the particle, and also its velocity using its time of flight between the laser beams. The individual sensors 16, 18 can therefore, in addition to flow, also measure the number and size distribution of particles passing through a given volume and therefore the average particle flux. Other sensors work in different ways. For example a simple measurement of flow speed may be made in order to infer the particle flux.

In other embodiments fluorescence sensors measuring chlorophyll a concentration may be employed to estimate algal particle flux and thus calculate clearance rate.

Additionally or alternatively micro-sensors for oxygen could be used. Such sensors detect the change in oxygen between in-flowing water and out-flowing water. This gives a measure of the organism's metabolic rate at any given time. Metabolic rate and thus oxygen use tends to increase in the presence of increasing pollution Oxygen micro-sensors and fluorescence sensors can be used alone or together, especially in water containing sand or clay particles. The sensors may be placed in the inflow/outflow currents or may be focussed on them, depending on the type of sensor.

Figure 3:
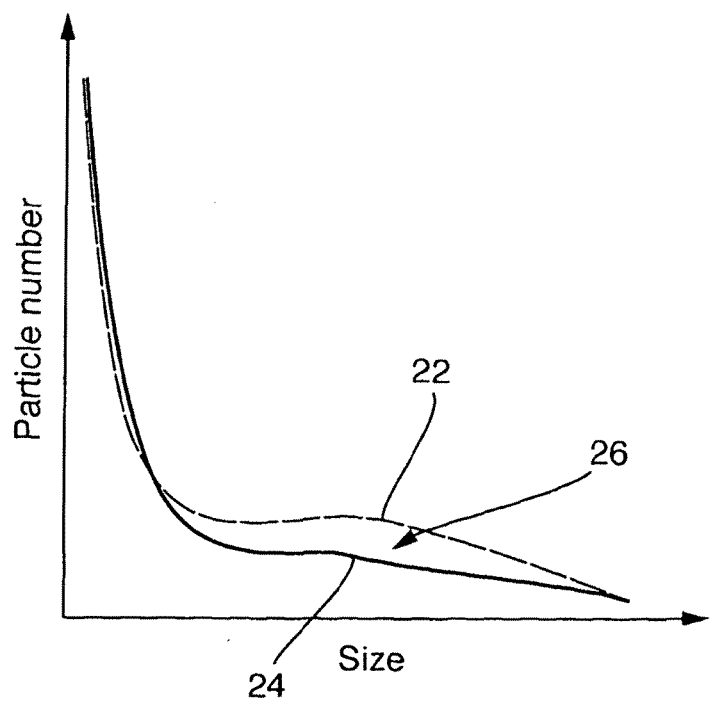
FIG. 3 is a graph showing how food uptake rate is calculated.

FIG. 3 shows two plots 22, 24. The upper plot 22 corresponds to the size distribution of particles measured by the inhalant sensor 16 and the lower plot 24 corresponds to the size distribution of particles measured by the exhalant sensor 18. These plots can be generated by integrating the measured flux over a given time.

The area between the plots 26 represents the food uptake rate or clearance rate of the mussel 2. By measuring the food uptake rate, the scope for growth of the mussel can be estimated relatively accurately. Thus successive measurements for a given individual organism can be used to indicate changes in the scope for growth which can indicate changing levels of aquatic pollution. The sensors 16, 18 may transmit raw data to a remote computer for processing and analysis or the data may be stored and/or processed locally in the submersed biosensor unit.

Figure 4:
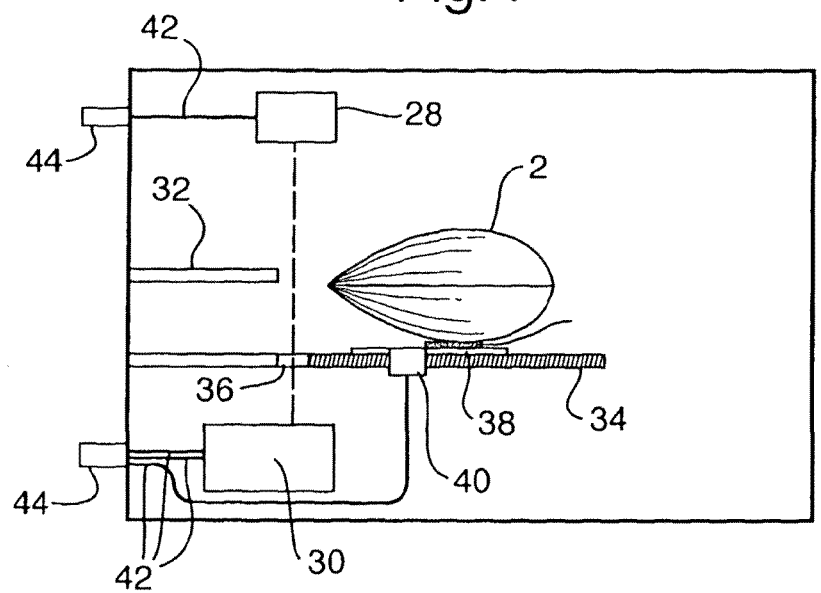
FIG. 4 is a schematic drawing of part of a biosensor unit according to an embodiment of the invention showing how apical growth can also be measured.
Figure 5:
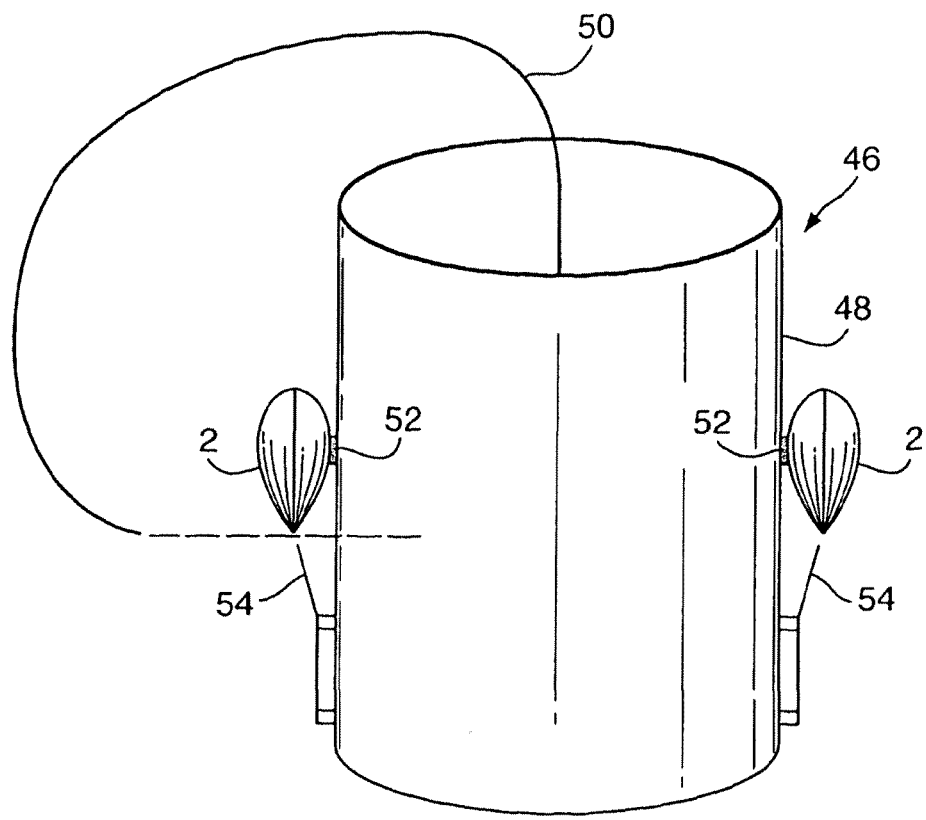
FIG. 5 is a schematic drawing of a biosensor unit which is adapted to simultaneously monitor the clearance rate and growth rate of a plurality of sessile organisms.

FIG. 4 shows, schematically, how apical growth of the mussel 2 can also be measured.

Within the biosensor unit are disposed a He—Ne laser source 28, CCD light detector 30 and a blade 32. The laser source 28 is arranged such that the beam it generates is aligned to pass immediately adjacent the edge of blade 32.

Also within biosensor unit 1 are disposed two parallel threaded tracks 34 carrying between them a fixed beam stop 36 and a mobile carriage 10. The carriage 10 is attached to a drive motor 40 operation of which causes the carriage 10 to move towards or away from the blade 32. The carriage 10 is provided with position location means (not shown) which provide a data signal indicating the relative spacing between the carriage 10 and the blade 32. The mussel 2 is mounted on the carriage 10 with the growing edge of the shell tip pointing towards the blade 32. The laser source 28, light detector 30 and drive motor 40 are provided with power and data transmission leads 42 to connectors 44.

In operation, the motor 40 is engaged to draw the mussel 2 towards the blade 32 until a predetermined light diffraction pattern (i.e. one having readily discernible dark and light spots) is detected by the detector 30. The average distance (d) between adjacent spots in the diffraction pattern is inversely proportional to the width of the slit (a), which can be calculated from the formula a=λ·s/d, where s is the vertical distance from the slit to the diffraction pattern and λ is the wavelength of the laser light.

After a set period of time (e.g. 24 hours), a further diffraction pattern is detected by the detector 30 and used to calculate the width of the slit. The reduction in slit width provides an indication of the apical growth of the mussel 2. Such measurements will generally be repeated over a period of several days (or, as appropriate, several months) until the apical tip of the mussel 2 is almost touching the blade 32 (i.e. when the diffraction pattern is almost diminished). At that point, the motor 40 is engaged to draw the mussel away from the blade 32 until an optimum diffraction pattern is once again obtained. The process may then be repeated to further monitor the growth rate of the mussel 2.

In an exemplary application of the embodiment set out above, the apparatus is set up to measure diffraction patterns over a range of slit apertures of 100-900 μm but to re-enlarge the aperture by moving the mussel carrier when the slit has been reduced to 200 μm. Under normal conditions in the summer with ample food (algae) in the in the water typical shell growth is of the order of 50 μm/day although can be as high as 100 μm/day. The aperture is typically re-enlarged on a weekly basis. In winter shell growth can be less than 1 μm/day and so adjustment needs only to be made at two-monthly intervals.

Referring to FIG. 6 there is shown a biosensor unit 46 in accordance with an embodiment of the invention. In this embodiment the biosensor unit comprises a transparent water impervious cylinder 48 having disposed therein various sensor units (not shown). These include particle flux sensors such as those shown in FIG. 1 and a light detector such as that shown in FIG. 4. The biosensor unit 46 also includes an optical fibre 50 connected to a source of laser light (not shown) positioned within the cylinder 48.

Mounted on the outer surface of the cylinder 46, using adhesive 52, are a plurality of mussels 2 and a plurality of plastic tabs 54. Each mussel 2 is mounted such that the growing edge of its shell tip is pointing towards a plastic tab 54. The optical fibre 50 and detector may be manipulated such that the laser beam is aligned to impinge on the gap between the edge of the plastic tab 54 and the tip of the mussel. The corresponding diffraction pattern is recorded. The laser-detector arrangement is then indexed round to the next organism to measure that gap. Of course the organisms could be moved (by rotating the cylinder) or each organism could be provided with its own detector.

Similarly a plurality of particle flux sensors is provided—one for each mussel 2 in the vicinity of its exhalant siphon. One or more further particle flux sensors is provided to determine the particle density in the common environment of the mussels 2 in order to establish the intake size distribution.

The mussels 2 are used individually to provide measurements of the effects of pollution by measuring growth and particle clearance rate for each one individually. In any given individual the growth and clearance rate will be altered from their established background levels (which may differ from one mussel to the next) in the presence of pollution. Thus by measuring the effect on individual mussels, an indication of pollution can be obtained from each.

Figure 6A:
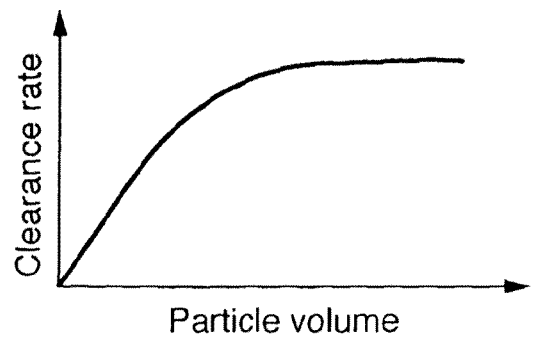
FIGS. 6a and 6b are plots showing respectively theoretical and measured relationships between clearance rate and particle volume.
Figure 6B:
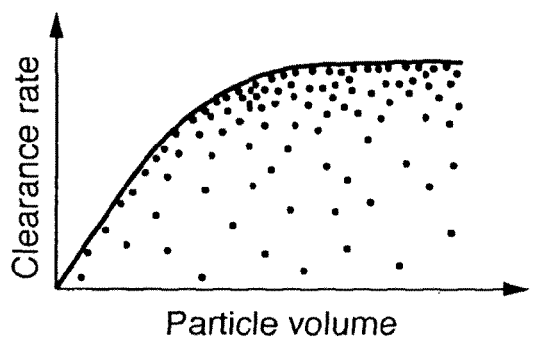

FIG. 6a shows schematically the theoretical relationship between particle clearance rate and particle volume for a particular organism—e.g. a mussel. FIG. 6b shows a representative plot of various clearance rate and particle volume data points 60 as might be actually measured. The scatter is partly accounted for by short-term opening and closing of the mussel; as the mussel closes, its clearance rate is diminished. The line 62 at the top represents the upper envelope of the data points 60 in respect of particle clearance rate. Clearly as more data points are measured, the more clearly this envelope will emerge. The envelope 62 approximates the theoretical relationship shown in FIG. 6a. The envelope 62 corresponds to the mussel being fully open.

Figure 6C:
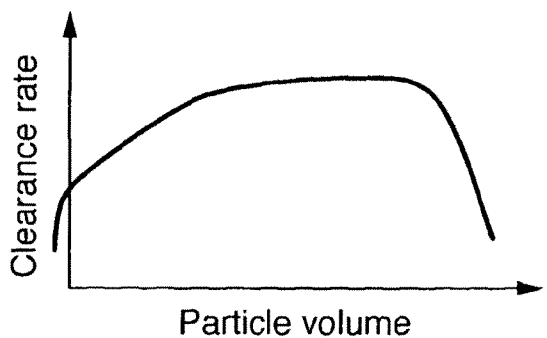
FIGS. 6c and 6d are plots showing respectively theoretical and measured relationships between clearance rate and temperature.
Figure 6D:
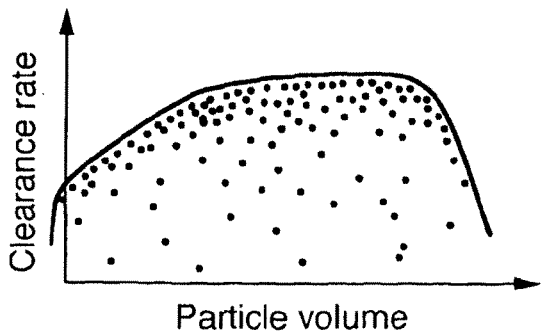

FIG. 6c shows a schematic theoretical relationship between temperature and particle clearance rate. Again as actual data points 64 are measured, an envelope curve 66 will emerge as shown in FIG. 6d.

Figure 7A:
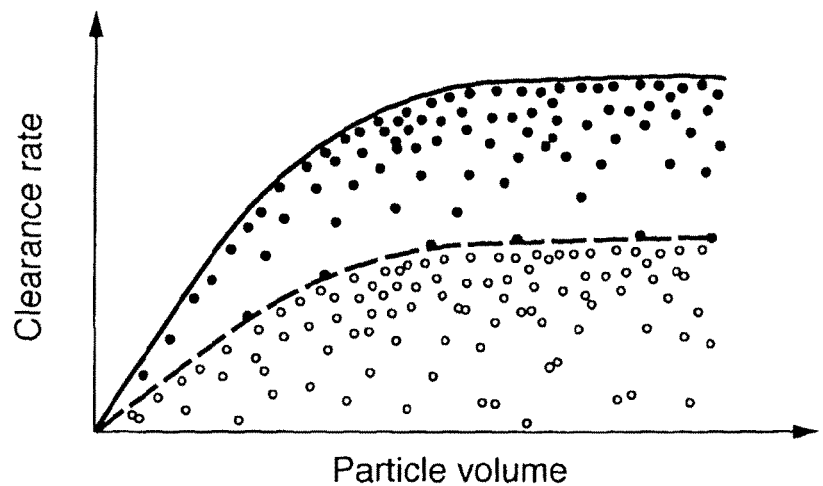
FIGS. 7a and 7b are plots of particle clearance rate against particle volume and temperature respectively showing the effect of pollution.

FIG. 7a shows the plot of FIG. 6b but with a second set of particle clearance rate/particle volume data points 68 (shown in lighter shading) superimposed representing measurements taken at a later time than the first set. It will be seen that the second set of data points has a lower envelope curve 70. This is a strong indicator that the individual organism to which the data relate has been exposed to aquatic pollution. Thus by measuring the shift in the envelope curve, the presence or increase in pollution between the time of the first measurement set and the time of the second measurement set can be detected.

Figure 7B:
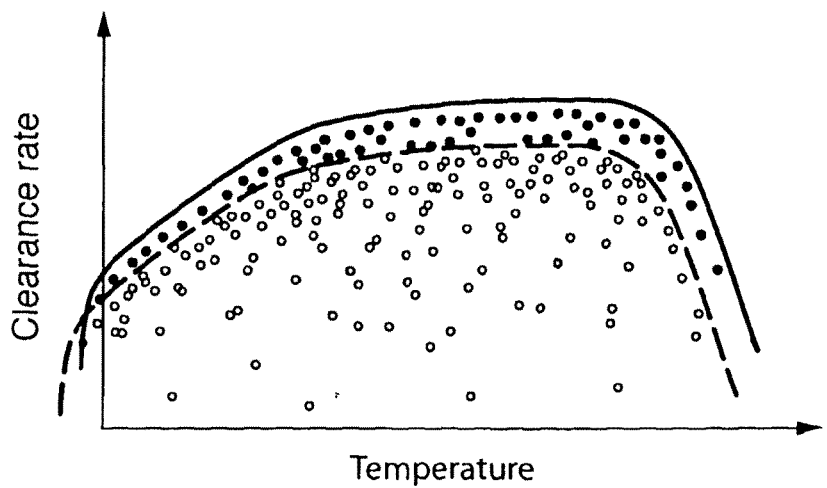

FIG. 7b shows that the particle clearance rate/temperature envelope curve exhibits a similar relationship in that it shifts downwards from the initial position 66 corresponding to the first measurements, to the later position 72 corresponding to the second set of measurements taken in the presence of pollution.

Figure 8:
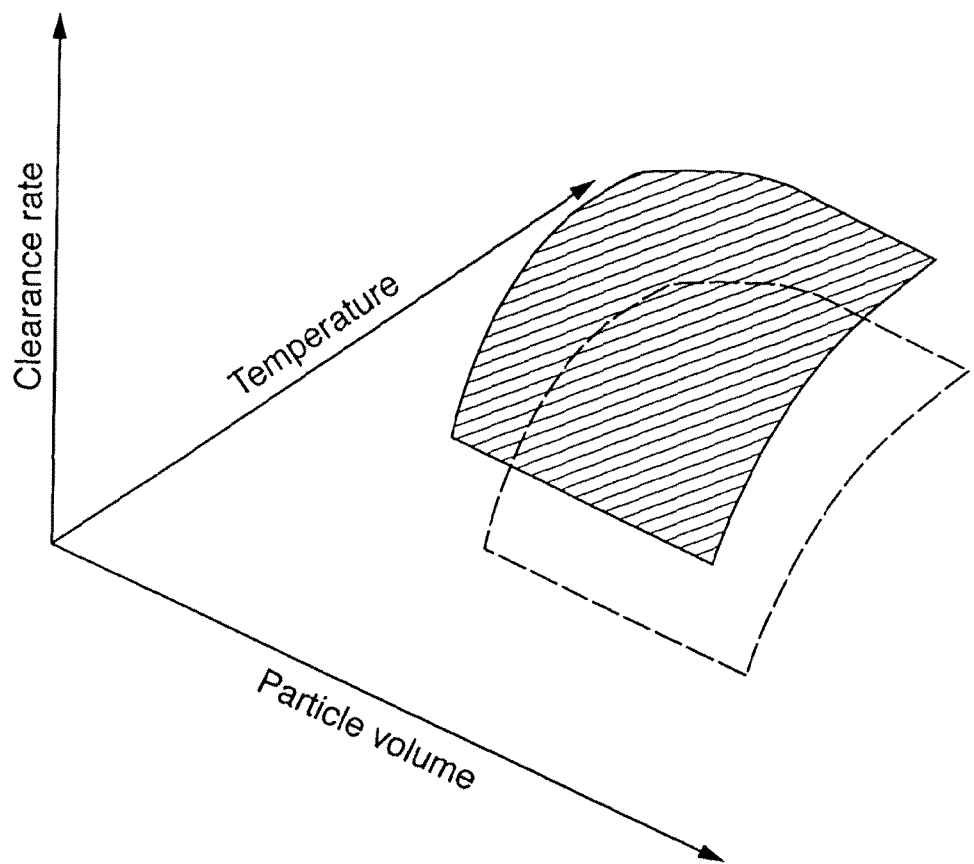
FIG. 8 is a three-dimensional plot of particle clearance rate against particle volume and temperature showing the effect of pollution.

FIG. 8 shows that the dependence of the particle clearance rate on particle volume and on temperature can be represented simultaneously using a three-dimensional plot. Here the data envelope is a surface which moves from an initial position 74 before pollution is introduced to a later position 76 after the introduction of pollution. Combining both parameters in this way can give a more reliable indicator.

At any point x-y point on this plot (i.e. for any combination of particle volume and temperature) a pollution effect index can be defined as the ratio of the heights of the two envelope surfaces in the corresponding vertical column.

Thus the pollution effect index based on clearance rate $PI_{CL} = CL_{max}/CL_{supp}$ where:

$CL_{max}$ is the maximum clearance rate (represented by the upper surface 74); and $CL_{supp}$ is the suppressed clearance rate (represented by the lower surface 76).

The value of $PI_{CL}$ may differ across the x-y plane but such variations are likely to be minimal over relatively small sections of the surfaces and under stable conditions. If necessary an average over a certain area could be taken.

Although this aspect of the invention is illustrated above using particle clearance rate (CL), similar relationships are observed for pumping rate (V) and growth rate (U). Thus in an analogous manner pollution indices may be defined:

$$PI_V = V_{max}/V_{supp}$$

$$PI_U = U_{max}/U_{supp}$$

A similar index can be defined for oxygen consumption although this will be inverted compared to those corresponding to particle clearance and growth rates due to the relative inverse dependency of oxygen consumption on pollution—i.e. as pollution increases so does oxygen consumption.

Different indices may be more sensitive to different types of pollution and thus one or more of these indices could be monitored as part of an aquatic pollution monitoring system.

The invention claimed is:

1. A method of monitoring an effect of pollution in an aquatic mass, said method comprising:
   - disposing in said aquatic mass a biosensor unit containing a living sessile organism;
   - performing a series of first measurements, of a flux of particles in said aquatic mass in a region adjacent a feeding orifice of said organism;
   - performing a series of second measurements, of a flux of particles in said aquatic mass in a region adjacent an excretion orifice of said organism; and
   - using said first and second measurements to calculate a particle clearance rate for said organism.

2. The method of claim 1 further comprising measuring a size distribution of said particles.

3. The method of claim 1 further comprising measuring a pumping rate of the organism.

4. The method of claim 3 further comprising determining the pumping rate using velocity vectors of particles carried in the aquatic mass.

5. The method of claim 1 further comprising measuring a water flow speed.

6. The method of claim 5 further comprising measuring a gape of the organism.

7. The method of claim 1 further comprising using a set of sensors continuously or frequently to measure water flow speed and periodically or less frequently also to determine particle density.

8. The method of claim 1 further comprising measuring parameters of individual particles.

9. The method of claim 8 further comprising using a laser particle detector.

10. The method of claim 1 further comprising measuring individual clearance rates for each of a plurality of organisms.

11. The method of claim 10 further comprising measuring a particle flux or density in a common environment of the organisms.

12. The method of claim 1 further comprising measuring a chlorophyll a fluorescence in a region of a feeding orifice and an excretion orifice of the organism respectively.

13. The method of claim 1 further comprising using at least one further sensor in association with the or each organism in order to detect a different pollution-dependent characteristic thereof.

14. The method of claim 1 wherein said organism is a sessile organism exhibiting apical growth, said method further comprising measuring said apical growth.

15. The method of claim 1 further comprising the steps of:
   - carrying out a series of first measurements of particle clearance rate during a first time period;
   - recording each of said first measurements with an associated measurement of a second parameter to give a series of first data points;
   - determining and recording a first upper envelope with respect to particle clearance rate for said first data points;
   - carrying out a series of second measurements of particle clearance rate during a second time period;
   - recording each of said second measurements with an associated measurement of a second parameter to give a series of second data points;
   - determining and recording a second upper envelope with respect to particle clearance rate for said second data points; and
   - comparing said first and second upper envelopes to determine the presence of pollution during said first or second time period.

16. The method of claim 1 further comprising the steps of:
   - carrying out a series of first measurements of growth rate of the organism during a first time period;
   - recording each of said first measurements with an associated measurement of a second parameter to give a series of first data points;
   - determining and recording a first upper envelope with respect to growth rate of the organism for said first data points;
   - carrying out a series of second measurements of growth rate of the organism during a second time period;
   - recording each of said second measurements with an associated measurement of a second parameter to give a series of second data points;
   - determining and recording a second upper envelope with respect to growth rate of the organism for said second data points; and
   - comparing said first and second upper envelopes to determine the presence of pollution during said first or second time period.

17. The method of claim 1 further comprising the steps of:
   - carrying out a series of first measurements of an oxygen consumption of the organism during a first time period;
   - recording each of said first measurements with an associated measurement of a second parameter to give a series of first data points;
   - determining and recording a first upper envelope with respect to the oxygen consumption of the organism for said first data points;
   - carrying out a series of second measurements of an oxygen consumption of the organism during a second time period;
   - recording each of said second measurements with an associated measurement of a second parameter to give a series of second data points;
   - determining and recording a second upper envelope with respect to the oxygen consumption of the organism for said second data points; and
   - comparing said first and second upper envelopes to determine the presence of pollution during said first or second time period.

18. A method of monitoring an effect of pollution in an aquatic mass comprising the steps of:
  placing a living sessile organism in said aquatic mass;
  carrying out a series of first measurements of a first parameter of said organism during a first time period;
  recording each of said first measurements with an associated measurement of a second parameter to give a series of first data points;
  determining and recording a first upper envelope with respect to said first parameter for said first data points;
  carrying out a series of second measurements of said first parameter of said organism during a second time period;
  recording each of said second measurements with an associated measurement of a second parameter to give a series of second data points;
  determining and recording a second upper envelope with respect to said first parameter for said second data points; and
  comparing said first and second upper envelopes to determine a presence of pollution during said first or second time period, wherein said first parameter comprises particle clearance rate, pumping rate, growth rate or oxygen consumption.

19. An apparatus for monitoring an effect of pollution in an aquatic mass, said apparatus comprising:
  a biosensor unit containing a living sessile organism;
  an arrangement for performing a series of first measurements of a flux of particles in said aquatic mass in a region adjacent a feeding orifice of said organism;
  an arrangement for performing a series of second measurements of a flux of particles in said aquatic mass in a region adjacent an excretion orifice of said organism; and
  an arrangement for calculating a particle clearance rate of said organism using said first and second measurements.

20. The apparatus of claim 19 further comprising one or more sensors configured to measure a size distribution of said particles.

21. The apparatus of claim 19 further comprising one or more sensors configured to measure a pumping rate of the organism.

22. The apparatus of claim 21 further comprising one or more sensors configured to measure velocity vectors of particles carried in the aquatic mass.

23. The apparatus of claim 19 further comprising one or more sensors for measuring a water flow speed.

24. The apparatus of claim 19 further comprising one or more sensors for measuring a gape of the organism.

25. The apparatus of claim 19 further comprising one or more sensors for measuring parameters of individual particles.

26. The apparatus of claim 25 further comprising a laser particle detector.

27. The apparatus of claim 19 further comprising one or more sensors for measuring individual clearance rates for each of a plurality of organisms.

28. The apparatus of claim 19 further comprising one or more sensors for measuring a particle flux or density in a common environment of the organism.

29. The apparatus of claim 19 further comprising one or more sensors for measuring a chlorophyll a fluorescence in a region of a feeding orifice and an excretion orifice of the organism respectively.

30. The apparatus of claim 19 further comprising a plurality of sessile organisms distributed around a rim of a disc or an outer surface of a cylinder.

31. The apparatus of claim 30 wherein each organism is provided with a detector to detect an exhaled particle flux or density or flow speed of the organism.

32. The apparatus of claim 30 wherein said cylinder is transparent.

33. The apparatus of claim 19, wherein the living sessile organism is a sessile organism exhibiting apical growth and the living sessile organism is bound to the apparatus, the apparatus further comprising an edge so as to form a gap between it and a tip of the sessile organism, an electromagnetic source arranged such that a beam therefrom impinges upon said gap to produce a diffraction pattern, and a corresponding electromagnetic detector arranged to detect said diffraction pattern and an arrangement for monitoring a change in said diffraction pattern over time which is indicative of a natural growth of the tip of said organism.

34. The apparatus of claim 19 further comprising a plurality of sensors associated with the organism.

35. The apparatus of claim 34 wherein said sensors are selected from a group comprising sensors for measuring water flow speed, particle flow speed, particle flux, chlorophyll a fluorescence, oxygen concentration and apical shell growth.

36. The apparatus of claim 19 further comprising a water sampler.

37. The apparatus of claim 19 further comprising a data transmitter for transmitting data to a remote receiver.

38. The apparatus of claim 19 further comprising one or more of the following monitors: a temperature monitor; a light monitor; a sound monitor; a salinity monitor; an alkalinity monitor; and a water-flow monitor.

* * * * *